United States Patent [19]
King et al.

[11] 3,944,572
[45] Mar. 16, 1976

[54] LACTONES

[75] Inventors: Ian Robert King; Francis R. F. Hardy, both of Luton, England

[73] Assignee: Laporte Industries Limited, Luton, England

[22] Filed: Apr. 5, 1974

[21] Appl. No.: 458,395

[30] Foreign Application Priority Data
Apr. 11, 1973 United Kingdom............... 17497/73

[52] U.S. Cl. ........................... 260/343.6; 260/526 N
[51] Int. Cl.² ......................................... C07D 307/32
[58] Field of Search ..................... 260/343.6, 526 N

[56] References Cited
UNITED STATES PATENTS

| | | | |
|---|---|---|---|
| 2,876,258 | 3/1959 | Phillips et al. .................. | 260/526 N |
| 3,037,052 | 5/1962 | Bortnick .......................... | 260/343 |

OTHER PUBLICATIONS

Ansell et al., Quarterly Reviews, 1964, pp. 211–225.

*Primary Examiner*—Anton H. Sutto
*Assistant Examiner*—Jane S. Myers
*Attorney, Agent, or Firm*—Larson, Taylor & Hinds

[57] ABSTRACT

A δ- or ε- lactone is heated in the vapour phase and the presence of a cracking catalyst to form a monounsaturated acyclic carboxylic acid. For example ε-caprolactone gives δ - ε hexenoic acid. This acid is then cyclised by heating with a strong protonating agent. In the example the product is γ-caprolactone or 4-hexanolactone.

6 Claims, No Drawings

LACTONES

The present invention relates to isomerisation and in particular to the production of γ- lactones by the isomerisation of δ- or ε-lactones.

It has hitherto been known to produce acyclic unsaturated carboxylic acids by heating ε- caprolactones to temperatures from at least 400°C to greater than 800°C, and such a process is disclosed in U.S. Pat. No. 2,876,258. It has also been disclosed in U.S. Pat. No. 3,037,052 that β, or γ, δ-acyclic unsaturated carboxylic acids may be cyclised to the corresponding γ- lactone by heating in the presence of a macro-reticular cation exchange resin in the dehydrated acid form. Other methods, also using strong protonating agents, of converting olefinic acids to γ-lactones are known and are described in 'Quarterly Reviews' 1964 page 211 – 255 (published by Chemical Society) by M. F. Ansell and M. H. Palmer.

According to the present invention there is provided a process for the production of a γ- lactone which comprises, (a) heating a δ- and/or ε-lactone in the vapour phase at a temperature below 400°C in the presence of a cracking catalyst to form a mono-unsaturated acyclic carboxylic acid and (b) cyclising the mono-unsaturated carboxylic acid by contacting it with a catalyst comprising a strong protonating agent.

It seems that the cracking catalyst should have a high surface area to be effective and we have found that zeolites and alumino silicates are satisfactory. Moreover refractory oxides may, in general, be used and alumina, silica and zirconia, particularly in the activated form, have proved very satisfactory.

Activated refractory oxide material is well known in the art to refer to an oxide which has been hydrated and calcined. A preferred refractory oxide is activated alumina such as may be purchased under the trade mark ACTAL from Laporte Industries Limited. It has been found that the grade of activated alumina sold as ACTAL 1 is particularly suitable. Normally the catalyst in the form of a catalyst bed is heated to and maintained at the desired temperature by independent heating means such as an electrical resistance element.

The feed lactone is preferably vapourised and preheated before being passed over the bed of catalyst. Preferably the temperature of the catalyst is from 300°C to 380°C. Advantageously water vapour is present in the catalyst zone since its presence has been found to suppress side reactions and lengthen the useful life of activated refractory oxide material catalysts. Conveniently the water vapour is metered into the feed lactone stream before it is vapourised.

By the terms γ-, δ- and ε- lactones are meant lactones having a total of 4, 5 and 6 carbon atoms respectively in the lactone ring.

Thus by the term ε- lactone is meant a compound or compounds each having the formula:

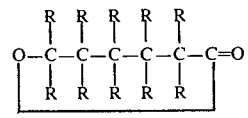

wherein each group R is any group selected from methyl, ethyl, n-propyl and iso-propyl groups and hydrogen, chlorine and bromine atoms, provided that the total number of carbon atoms in the formula does not exceed 12 and provided that there are no more than 2 halogen atoms in the formula.

Preferably the ε- lactone is ε-caprolactone, i.e. all the groups R are hydrogen, or a methyl ε- caprolactone, a mixture of isomeric methyl ε-caprolactones or a mixture of isomeric methyl ε-caprolactones with ε-caprolactones.

In the case of a δ- lactone the formula is:

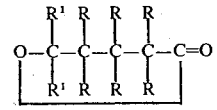

wherein R and $R^1$ have the meaning of R above, modified in that the maximum number of carbon atoms is 10. We prefer in fact to use a mono-methyl substituted δ- lactone, i.e. δ- caprolactone, conveniently the δ-caprolactone wherein the substitution is at $R^1$.

It has been found that heating a δ- or ε-lactone at a temperature of from 250°C to 400°C in the presence of an activated refractory oxide material catalyst may lead to a very high yield of unsaturated acid and for example, heating ε- caprolactone at 350°C in the presence of activated alumina gives between 60% and 80% by weight of hexenoic acid. In addition, there is normally a substantial yield (from 15% – 20 %) of γ- lactone at the end of this first stage. Thus the yield of useful products from the heating of a δ or ε- lactone may approach 100% of the lactone input.

The strong protonating agent may be one or more of a strong acid such as sulphuric acid, toluene-p-sulphonic acid, formic acid, oxalic acid or trifluoroacetic acid, a cation exchange resin in the free acid form, a strongly acidic mixture containing hydrogen ions such as hydrogen halides in acetic acid or a similar protonating substance. A preferred strong protonating agent is a cation exchange resin in the free acid form. The cation exchange resin is preferably a macro-reticular exchange resin such as that sold by Rohm and Haas as AMBERLYST 15. AMBERLYST is a registered Trade Mark.

According to another aspect of the present invention there is provided a process for the production of a γ- lactone which comprises cyclising an acyclic carboxylic acid in which an olefinic bond is present in the δ - ε position by contacting it with a cation exchange resin in the free acid form at a temperature of from 100°C to 200°C.

It will be understood from the above that the cyclising step may be carried out in the presence of γ-lactone. The unsaturated acyclic carboxylic acid is normally in the liquid phase and is conveniently contacted continuously in a column with the strong protonating agent which may be a liquid or a solid.

Preferably the temperature of the contacting is from 120°C to 160°C. The reaction with the strong protonating agent may result in a small amount of δ- lactone remaining or being formed and this may be removed from the γ- lactone by, for example, distillation and then recycled over the catalyst. Unreacted acid may also be recovered by distillation and recycled.

The present invention also provides γ- lactones whenever made according to the process of the present invention. The γ-lactones are particularly useful as solvents for certain polymeric materials such as polystyrene, cellulose butyrate acetate and polyurethane and as flavours.

A specific embodiment of the present invention will now be described by way of example only.

EXAMPLE

A tubular glass reactor equipped with electrical heating elements was packed with 120 mls of 7 – 10 mesh BSS activated alumina (sold as ACTAL 1 by General Chemicals Division, Widnes of Laporte Industries Limited). Mixtures of ε-caprolactone and water were fed from a metering pump to a heated vapouriser and then to the reactor maintained at 350°C. The feed rate of ε-caprolactone was kept constant as the amount of water was varied. The reaction product was condensed and analysed by titrimetry and gas liquid chromatography. The results are given in Table I.

Table I

| RUN NO. | MOLAR RATIO WATER TO ε-CAPRO-LACTONE | RESIDENCE TIME (SECS.) | YIELD OF HEXENOIC ACID % BY WEIGHT | YIELD OF γ-CAPRO-LACTONE % BY WEIGHT | MASS RECOVERY % BY WEIGHT |
|---|---|---|---|---|---|
| 1 | 39:1 | 2.25 | 81.0 | 16.2 | 99.9 |
| 2 | 9:1 | 9.0 | 71.2 | 17.5 | 98.1 |
| 3 | 1:1 | 45.0 | 62.3 | 16.8 | 97.3 |

The product of Run 2 was separately fed to a column containing AMBERLYST 15 cation exchange resin in the H$^+$ form (100 mls) at a rate of about 0.5 bed volumes per hour. The column was electrically heated and its temperature maintained at 140°C. The column effluent was analysed for γ- and ε-caprolactones and for hexenoic acid. The results are given in Table II. About 80 bed volumes of product were collected with little or no change in the composition.

Table II

| PRODUCT FROM RUN NO. | TOTAL ACID, AS HEXENOIC ACID, % BY WEIGHT | YIELD OF δ-CAPRO-LACTONE % BY WEIGHT | YIELD OF γ-CAPRO-LACTONE % BY WEIGHT |
|---|---|---|---|
| 2 | 11% | 1% | 87% |

We claim:

1. A process for the production of a γ-caprolactone comprising
   a. heating an ε-caprolactone in the vapour phase at a temperature below 400°C in the presence of a cracking catalyst selected from the group consisting of aluminosilicates and refractory oxides to form a mono-unsaturated acyclic carboxylic acid and
   b. cyclising said mono-unsaturated acyclic carboxylic acid by contacting it with a catalyst comprising a strong protonating agent, selected from the group consisting of strong acids, cation exchange resins in the free acid form, and strongly acidic mixtures containing hydrogen ions.

2. The process of claim 1, wherein the cracking catalyst is activated alumina.

3. The process of claim 1, wherein the feed lactone is passed over the cracking catalyst whilst it is maintained at a temperature between 300°C and 380°C.

4. The process of claim 1, wherein water vapour is present in the catalyst zone.

5. The process of claim 1, wherein the feed lactone is ε-caprolactone or a methyl ε-caprolactone.

6. The process of claim 1, wherein the unsaturated acyclic carboxylic acid is in the liquid phase and is contacted continuously in a column with the strong protonating agent which is a solid, the cyclising being effected at a temperature in the range 120°C to 160°C.

* * * * *